US011026449B2

(12) United States Patent
Mironov

(10) Patent No.: US 11,026,449 B2
(45) Date of Patent: Jun. 8, 2021

(54) SACHET OF AEROSOL-FORMING SUBSTRATE, METHOD OF MANUFACTURING SAME, AND AEROSOL-GENERATING DEVICE FOR USE WITH SACHET

(71) Applicant: Philip Morris Products S.A., Neuchatel (CH)

(72) Inventor: Oleg Mironov, Neuchatel (CH)

(73) Assignee: Philip Morris Products S.A., Neuchatel (CH)

( * ) Notice: Subject to any disclaimer, the term of this patent is extended or adjusted under 35 U.S.C. 154(b) by 577 days.

(21) Appl. No.: 15/563,134

(22) PCT Filed: Apr. 7, 2016

(86) PCT No.: PCT/EP2016/057672
§ 371 (c)(1),
(2) Date: Sep. 29, 2017

(87) PCT Pub. No.: WO2016/162446
PCT Pub. Date: Oct. 13, 2016

(65) Prior Publication Data
US 2018/0084831 A1    Mar. 29, 2018

(30) Foreign Application Priority Data

Apr. 7, 2015    (EP) .................................... 15162640

(51) Int. Cl.
*A24F 47/00*    (2020.01)
*A61M 11/04*    (2006.01)
*A61M 15/06*    (2006.01)

(52) U.S. Cl.
CPC ......... *A24F 47/008* (2013.01); *A61M 11/042* (2014.02); *A61M 15/06* (2013.01);
(Continued)

(58) Field of Classification Search
CPC ... A24F 47/008; A61M 11/042; A61M 15/06; A61M 2205/3653; A61M 2205/8206
See application file for complete search history.

(56) References Cited

U.S. PATENT DOCUMENTS

| 4,922,901 A | 5/1990 | Brooks et al. |
| 4,981,522 A | 1/1991 | Nichols et al. |

(Continued)

FOREIGN PATENT DOCUMENTS

| CN | 201067079 Y | 6/2008 |
| CN | 103781375 A | 5/2014 |

(Continued)

OTHER PUBLICATIONS

International Search Report and Written Opinion dated Jul. 12, 2016 in PCT/EP2016/057672, filed Apr. 7, 2016.

(Continued)

*Primary Examiner* — Kendra D Carter
*Assistant Examiner* — Jonathan S Paciorek
(74) *Attorney, Agent, or Firm* — Oblon, McClelland, Maier & Neustadt, L.L.P.

(57) ABSTRACT

There is provided a sachet of aerosol-forming substrate for an electrically heated aerosol-generating device, the sachet including an aerosol-forming substrate disposed within the sachet, and an electrical heater element including first and second electrically conductive portions, the electrical heater element being disposed within the sachet and in direct contact with the aerosol-forming substrate, and the first and the second electrically conductive portions are configured to connect the electrical heater element with an external power supply. An electrically operated aerosol-generating device for a sachet is also provided. And, a method of manufacturing a sachet is provided.

6 Claims, 3 Drawing Sheets

(52) U.S. Cl.
CPC ............... *A61M 2205/3653* (2013.01); *A61M 2205/8206* (2013.01)

(56) References Cited

U.S. PATENT DOCUMENTS

| | | | |
|---|---|---|---|
| 5,067,500 | A | 11/1991 | Keritsis |
| 5,144,962 | A | 9/1992 | Counts et al. |
| 5,322,075 | A | 6/1994 | Deevi et al. |
| 5,479,948 | A * | 1/1996 | Counts .................. A24F 47/008 131/194 |
| 2011/0126848 | A1 | 6/2011 | Zuber et al. |
| 2012/0055493 | A1 | 3/2012 | Novak, III et al. |
| 2014/0060554 | A1 | 3/2014 | Collett et al. |
| 2015/0027459 | A1 | 1/2015 | Collett et al. |
| 2015/0040929 | A1 | 2/2015 | Hon |
| 2015/0272226 | A1 | 10/2015 | Zuber et al. |
| 2016/0174613 | A1 | 6/2016 | Zuber et al. |

FOREIGN PATENT DOCUMENTS

| | | |
|---|---|---|
| CN | 103859596 A | 6/2014 |
| CN | 103929988 A | 7/2014 |
| CN | 104023574 A | 9/2014 |
| EP | 0 395 291 A2 | 10/1990 |
| EP | 0 430 559 A2 | 6/1991 |
| EP | 0 612 221 B1 | 11/1999 |
| EP | 2 266 424 A1 | 12/2010 |
| EP | 2 327 318 A1 | 6/2011 |
| EP | 2 700 324 A1 | 2/2014 |
| GB | 2515992 A | 1/2015 |
| JP | H8-511966 A | 12/1996 |
| JP | 2011-505874 A | 3/2011 |
| JP | 2013-523115 A | 6/2013 |
| RU | 2 268 631 C2 | 1/2006 |
| WO | WO 2010/095660 A1 | 8/2010 |
| WO | WO 2011/050964 A1 | 5/2011 |
| WO | WO 2013/009883 A1 | 1/2013 |
| WO | WO 2013/159245 A1 | 10/2013 |
| WO | WO 2014/140087 A1 | 9/2014 |
| WO | WO 2014/160055 A1 | 10/2014 |
| WO | WO 2015/101479 A1 | 7/2015 |
| WO | WO 2015/117702 A1 | 8/2015 |
| WO | WO 2016/096927 A1 | 6/2016 |

OTHER PUBLICATIONS

Combined Chinese Office Action and Search Report dated Sep. 27, 2019, in Patent Application No. 201680017045.7 (with English translation), citing documents AO-AU therein, 12 pages.

Office Action dated Apr. 20, 2020 in corresponding Japanese Patent Application No. 2017-551171, 3 pages.

Combined Office Action and Search Report dated Aug. 29, 2019 in Russian Patent Application No. 2017134345, citing document AO therein, 18 pages (with English translation and English translation of categories of cited documents).

Japanese Decision to Grant dated Jan. 25, 2021 in corresponding Japanese Patent Application No. 2017-551171 (with English translation), citing document AO therein, 5 pages.

* cited by examiner

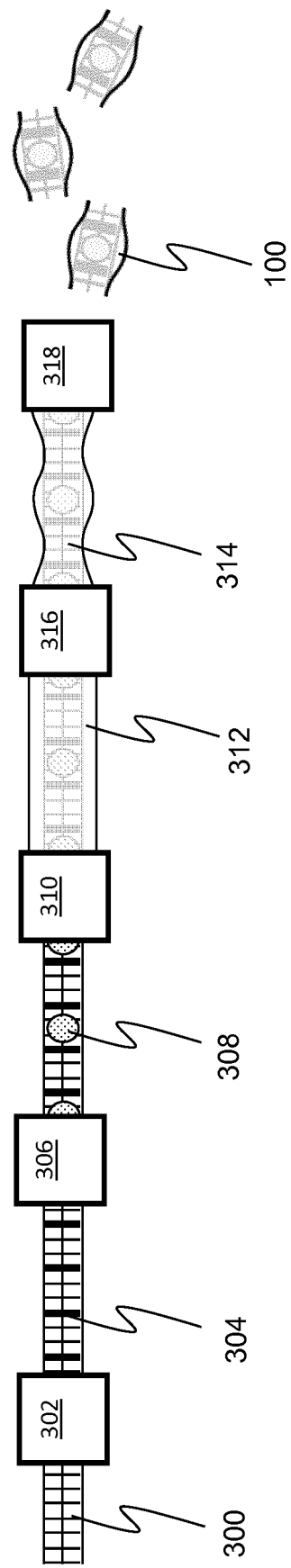

SACHET OF AEROSOL-FORMING SUBSTRATE, METHOD OF MANUFACTURING SAME, AND AEROSOL-GENERATING DEVICE FOR USE WITH SACHET

The present invention relates to a sachet of aerosol-forming substrate for use in an electrically heated aerosol-generating device. In particular, the invention relates to such a sachet comprising an electrical heater element. The invention further relates to an aerosol-generating device for use with the sachet of the present invention.

Electrically heated smoking systems typically include a power supply, such as a battery, connected to a heater to heat an aerosol-forming substrate, to form the aerosol which is provided to the smoker. In operation, these electrically heated smoking systems typically provide a high power pulse to the heater to provide the temperature range desired for operation and to release the volatile compounds. Electrically heated smoking systems may be reusable and may be arranged to receive a disposable smoking article containing the aerosol-forming substrate to form the aerosol. Alternatively, loose tobacco may be provided adjacent the electrical heater. Where loose tobacco is used, typically the user fills a cavity with the required amount of tobacco before using the device. The loose tobacco is then heated to a temperature sufficient to volatilise the desirable volatile compounds in the tobacco without reaching a temperature sufficient for combustion of the tobacco.

Such systems produce highly varied results depending on many factors only in the control of the user, such as the specific properties, and type, of the tobacco used, the quantity of tobacco placed in the cavity, and how much the user compresses the tobacco when providing it in the cavity.

In addition, the tobacco placed in the cavity is in direct contact with the high temperature surface heated by the electrical heater, or in some cases in direct contact with the heater itself. This direct contact may result in burnt tobacco residue on the surface and heater which can require regular cleaning.

It would therefore be desirable to reduce the variability, and increase the quality of the aerosol generated by such devices while increasing the hygiene and decreasing the amount of cleaning required.

According to a first aspect of the present invention, there is provided a sachet of aerosol-forming substrate for use in an electrically heated aerosol-generating device. The sachet comprises an aerosol-forming substrate within the sachet, and an electrical heater element comprising first and second electrically conductive portions. The electrical heater element is within the sachet and in direct contact with the aerosol-forming substrate, and the first and second electrically conductive portions are configured to connect the electrical heater element with an external power supply.

According to a second aspect of the present invention, there is provided a sachet of aerosol-forming substrate for use in an electrically heated aerosol-generating device. The sachet comprises: a container; an aerosol-forming substrate, within the container; and an electrical heater element comprising first and second electrically conductive portions. The electrical heating means is within the container and in direct contact with the aerosol-forming substrate, and the first and second electrically conductive portions are configured to connect the heater element with an external power supply.

Advantageously, providing a consumable sachet comprising an aerosol-forming substrate and an integrated heater both reduces the variability, and increases the quality of the aerosol generated, and provides a disposable heater which therefore does not require cleaning. Such a sachet also enables the aerosol-generating device which uses the sachet to be more durable and require less maintenance.

In addition, by providing the integrated electrical heater element the maximum distance between the heater element and the aerosol-forming substrate may be reduced, and thus the efficiency of the device using the sachet may be increased. More efficient heating of the aerosol-forming substrate enables less substrate to be provided to produce the same amount of aerosol.

Preferably, the first and second electrically conductive portions are contact portions, and may be external to the sachet or the container. By providing the contact portions external to the sachet or the container, the electrical connection between the heater element and an external power supply may be made more easily. The contact portions are preferably provided at first and second ends of the sachet or the container, and the aerosol-forming substrate is preferably provided at a position between the first contact portion and the second contact portion.

The first and second electrically conductive portions may have a length such that they extend across substantially the entire width of the sachet. The electrically conductive contact portions may have a width of between about 0.5 mm and about 3 mm, preferably between about 0.5 mm and about 2 mm.

Preferably, the electrical heater element comprises a plurality of electrically conductive filaments connected to the first and second electrically conductive contact portions. The electrical resistance of the electrically conductive filaments may be at least two orders of magnitude greater than the electrical resistance of the electrically conductive contact portions. This ensures that the heat generated by passing current through the heater element is localised to the electrically conductive filaments. It is advantageous to have a low overall resistance for the heater element if the system is powered by a battery. Minimizing parasitic losses between the electrical contacts and the filaments is also desirable to minimize parasitic power losses. A low resistance, high current system allows for the delivery of high power to the heater element. This allows the heater element to heat the electrically conductive filaments to a desired temperature quickly.

The plurality of electrically conductive filaments may form a mesh or array of filaments or may comprise a woven or non-woven fabric. The electrical resistance of the mesh, array or fabric of electrically conductive filaments of the heater element is preferably between about 0.3Ω and about 4Ω. More preferably, the electrical resistance of the mesh, array or fabric of electrically conductive filaments is between about 1Ω and about 3Ω.

The filaments may have a diameter between about 10 μm and about 50 μm, preferably between about 15 μm and about 30 μm.

The mesh or array of filaments may have a length of between about 3 mm and about 10 mm and a width of between about 2 mm and about 8 mm. In one example, the mesh or array of filaments has a length of about 5 mm and a width of about 3 mm. In this example, the mesh or array has around 35 filaments.

The material forming the electrically conductive contact portions may have an electrical resistivity of between about $10\times10^{-3}$ Ωm and about $20\times10^{-3}$ Ωm.

The electrically conductive filaments may be provided with a first density of filaments to form the heating element, and a second density of filaments to form the electrically conductive contact portions, the second density being greater than the first density. Preferably, the densities are number densities. By increasing the density of the filaments, the effective cross-sectional area of the contact portions is increased. As will be appreciated, the resistance of a conductor is inversely proportional to the cross-sectional area of the conductor.

The first density of filaments may be such that the heater mesh has a mesh size of between about 100 Mesh US (about 100 filaments per inch) and about 400 Mesh US (about 400 filaments per inch). The heater mesh may have a mesh size of between about 100 Mesh US (about 100 filaments per inch) and about 200 Mesh US (about 400 filaments per inch).

The electrically conductive filaments are preferably carbon fibres. The electrically conductive filaments may be any other suitable material such as metal, such as stainless steel.

The heater element may comprise at least one filament made from a first material and at least one filament made from a second material different from the first material. This may be beneficial for electrical or mechanical reasons. For example, one or more of the filaments may be formed from a material having a resistance that varies significantly with temperature, such as an iron aluminium alloy. This allows a measure of resistance of the filaments to be used to determine temperature or changes in temperature. This can be used for controlling heater temperature to keep it within a desired temperature range.

The sachet may comprise at least two electrical heater elements, the first electrical heater element disposed on a first side of the aerosol-forming substrate, and the second electrical heater element disposed on a second side of the aerosol-forming substrate. Advantageously, providing two heater elements in the sachet may yet further increase the efficiency by further reducing the maximum distance between the aerosol-forming substrate and the heat source.

The sachet or the container may be a hollow tube. The hollow tube may be formed from a flexible foil material. The aerosol-forming substrate and the heater element is provided within the hollow tube. The hollow tube is sealed at each end to form a sealed sachet. The hollow tube may be heat sealed, or sealed with adhesive. Where the electrically conductive contact portions are provided external to the sachet or the container, the heater element may extend through the sealed ends, the contact portions being coupled to the heater element external to the sachet or the container.

The material forming the sachet or the container may be substantially gas-impermeable. The sachet or the container may be formed from a foil material. The foil material is preferably flexible. The foil material is preferably a heat resistant polymer. Preferably the material is heat resistant up to about 250 degrees Celsius, or more preferably up to about 265 degrees Celsius. The heat resistance polymer may be Nylon 6,6 (Poly(hexamethylene adipamide)). Advantageously, forming the sachet or the container from material which is substantially gas-impermeable may improve the shelf-life of the sachet.

Alternatively, the material forming the sachet or the container may be permeable. The sachet may be formed from a mesh. The mesh is preferably porous to the generated aerosol, and enables the aerosol to be released from the sachet with causing condensation. The mesh may be formed by any suitable process, such as weaving the material, or by cutting using a toothed roller or the like, and then expanding the material by providing a force perpendicular to the axis of the toothed rollers.

The permeable sachet may be formed from any suitable material which is capable of resisting the high temperature during use, without combusting or imparting undesirable flavours into the aerosol. In particular, the natural fibres sisal and ramie are particularly appropriate for forming the sachet. Alternatively, the sachet may be formed from ceramic fibres or metal.

The material used to form the sachet may be between about 50 microns and about 300 microns in thickness. The fibre size of the material used to form the sachet may be between about 10 microns and about 30 microns.

The sachet or the sachet container may be any suitable shape and size. In some embodiments, in a first direction, the cross-sectional the shape of the sachet or the container is one of: an oval; a circle; a rectangle; a square; and a triangle. The cross-sectional shape, in a second direction perpendicular to the first direction, may be one of: a rectangle; a triangle a circle; and an oval.

As used herein, the term 'aerosol-forming substrate' is used to describe a substrate capable of releasing upon heating volatile compounds, which can form an aerosol. The volatile compounds are released by heating the aerosol-forming substrate. The aerosols generated from aerosol-forming substrates according to the invention may be visible or invisible and may include vapours (for example, fine particles of substances, which are in a gaseous state, that are ordinarily liquid or solid at room temperature) as well as gases and liquid droplets of condensed vapours.

The aerosol-forming substrate may be solid or liquid or comprise both solid and liquid components. In a preferred embodiment, the aerosol-forming substrate is solid.

The aerosol-forming substrate may comprise nicotine. The nicotine containing aerosol-forming substrate may be a nicotine salt matrix. The aerosol-forming substrate may comprise plant-based material. The aerosol-forming substrate may comprise tobacco, and preferably the tobacco containing material contains volatile tobacco flavour compounds, which are released from the aerosol-forming substrate upon heating. The aerosol-forming substrate may comprise homogenised tobacco material.

The aerosol-forming substrate may comprise tobacco and an aerosol-former. The tobacco may be one or more of: pipe tobacco; cut filler; reconstituted tobacco; and homogenised tobacco.

The aerosol-forming substrate preferably comprises: homogenised tobacco material; aerosol-former; and water. Providing homogenised tobacco material improves the aerosol generation, the nicotine content and the flavour profile. This is because the process of making the homogenised tobacco involves grinding tobacco leaf which enables the release of nicotine and flavours upon heating much more effectively.

Homogenised tobacco material may be formed by agglomerating particulate tobacco. Where present, the homogenised tobacco material may have an aerosol-former content of equal to or greater than 5% on a dry weight basis, and preferably between greater than 5% and 30% by weight on a dry weight basis.

The aerosol-forming substrate may alternatively comprise a non-tobacco-containing material. The aerosol-forming substrate may comprise homogenised plant-based material.

The aerosol-forming substrate may comprise at least one aerosol-former. The aerosol-former may be any suitable known compound or mixture of compounds that, in use, facilitates formation of a dense and stable aerosol and that is substantially resistant to thermal degradation at the operating temperature of the aerosol-generating device. Suitable aerosol-formers are well known in the art and include, but are not limited to: polyhydric alcohols, such as triethylene glycol, 1,3-butanediol and glycerine; esters of polyhydric alcohols, such as glycerol mono-, di- or triacetate; and aliphatic esters of mono-, di- or polycarboxylic acids, such as dimethyl dodecanedioate and dimethyl tetradecanedioate. Particularly preferred aerosol formers are polyhydric alcohols or mixtures thereof, such as triethylene glycol, 1,3-butanediol and, most preferred, glycerine.

The aerosol-forming substrate may comprise other additives and ingredients, such as flavourants.

The aerosol-forming substrate preferably comprises nicotine and at least one aerosol-former. In a particularly preferred embodiment, the aerosol-former is glycerine.

According to a third aspect of the present invention, there is provided an electrically operated aerosol-generating device. The device comprises: a power supply; electronic control circuitry; a cavity configured to receive a sachet of aerosol-forming substrate as described herein, in accordance with any of the embodiments of the first or second aspects of the present invention; a sachet retainer for retaining the sachet in the cavity; and electrical contacts disposed adjacent the cavity, and configured to allow electrically conductive portions of an electrical heater element of a sachet to be electrically connected to the power supply. The sachet retainer is configured to maintain electrical contact between the electrical heater element and the electrical contacts.

The sachet retainer advantageously enables the user to easily insert a sachet, but ensures that it is both mechanically and electrically securely coupled to the device.

The electrically operated aerosol-generating device may further comprise at least one piercing element configured to pierce a sachet of aerosol-forming substrate when the sachet is received in the cavity. The electrically operated aerosol-generating device may further comprise a first set of at least one piercing element and a second set of at least one piercing element, wherein the first set is configured to pierce a first side of a sachet and the second set is configured to pierce a second side of a sachet to form an airflow pathway through the sachet. In this way, the aerosol generated when the sachet is heater by the heater element is entrained in the airflow as it passes through the sachet.

Where provided, the or each piercing element may be hollow, such that an airflow pathway is formed through the piercing element and sachet. Alternatively, the piercing element may comprise a piercing portion and a shaft portion, the piercing portion having a cross-sectional area greater than the cross-sectional area of the shaft portion. When a sachet is received in the cavity, and pierced by the or each piercing element, the piercing portion is configured to extend into the sachet. In this way, an airflow pathway is formed around the shaft portion and through the sachet.

The electrical contacts disposed adjacent the cavity may be elongate. The elongate contacts are preferably configured to extend substantially along the entire length of the electrically conductive contact portions of the sachet. Increasing the contact area between the elongate contacts and the electrically conductive contact portions advantageously reduces the parasitic power losses by reducing the resistance at that connection.

Alternatively, where the electrically conductive portions of the sachet are not external to the sachet or the sachet container, the electrical contacts disposed adjacent the cavity may comprise one or more piercing elements. The piercing elements may pierce the sachet when the sachet is received in the cavity to make contact with the electrically conductive portions within the sachet. The electrically conductive portions of the heater element may be the heater filaments, and in this case the electrical contacts disposed adjacent the cavity are configured to electrically contact the filaments such that the electrical resistance is significantly lower than the electrical resistance of the remaining portions of the filaments. Preferably the electrical resistance is at least an order of magnitude lower to ensure there is minimal heating in the region adjacent the electrical contacts. More preferably, the electrical resistance is at least two orders of magnitude lower.

Preferably, the cavity is an internal cavity within an outer housing the device. The cavity may have a size and shape suitable for receiving the entire sachet, or alternatively only a portion of the sachet. The cross-sectional size and shape of the cavity opening is preferably substantially the same as the cross-sectional size and shape of the sachet.

The sachet retainer may comprise a lid movable between a first position in which a sachet can be inserted into the cavity, and a second position in which the sachet is retained in the cavity. The lid may be hinged to the main body of the device. The hinged lid may be hinged at a first end of the lid, the second end of the lid comprising a mouthpiece. The lid may comprise at least one piercing element. In this way a mechanical advantage may be provided to enable the or each, where provided, piercing element to more easily, that is requiring less force, pierce the sachet. The lid may be retained in the second position by any suitable means, such as magnets such as neodymium magnets, or a releasable catch.

Alternatively, the lid may be slidably engaged on the device. In a yet further alternative, the lid may comprise a screw thread, and the main body of the device may comprise a corresponding screw thread such that the lid can be screwed onto the main body to retain the lid on the device and thus the sachet within the cavity.

The lid may comprise a cavity configured to combine with the cavity for receiving the sachet to form a cavity which encloses the sachet.

The aerosol-generating device preferably comprises at least one air inlet, at least one air outlet, and an airflow pathway extending between the at least one air inlet and the at least one air outlet.

The power supply may be a battery, and may be a rechargeable battery configured for many cycles of charge and discharge. The battery may be a Lithium based battery, for example a Lithium-Cobalt, a Lithium-Iron-Phosphate, a Lithium Titanate or a Lithium-Polymer battery. The battery may alternatively be a Nickel-metal hydride battery or a Nickel cadmium battery. The battery capacity is preferably selected to allow for multiple uses by the user before requiring recharging. The capacity of the battery is preferably sufficient for a minimum of 20 uses by the user before recharging is required.

The aerosol-generating device comprises control circuitry. The control circuitry is preferably configured to supply power from the power supply to the at least one heater of the sachet. The control circuitry is preferably further configured to maintain the temperature of the at least one heater at an operating temperature of between about 100 degrees C. to 350 degrees C., more preferably 180 degrees C. and about 260 degrees C., and most preferably between about 220 degrees C. and about 240 degrees C. The aerosol-forming substrate may act as an insulator between the at least one heater and the sachet material or the sachet container material. In this way, the temperature of the sachet material or the sachet container material is preferably maintained below about 265 degrees C., more preferably below about 200 degrees C., and yet more preferably below about 150 degrees C.

The control circuitry may comprise a microprocessor, which may be a programmable microprocessor, a microcontroller, or an application specific integrated chip (ASIC) or other electronic circuitry capable of providing control. The electric circuitry may comprise further electronic components.

The aerosol-generating device may comprise a puff detector in communication with the control circuitry. The puff detector is preferably configured to detect when a user draws on the aerosol-generating device mouthpiece. The control electronics are preferably further configured to control power to the at least one heating element in dependence on the input from the puff detector.

Power may be supplied to the heater element continuously following activation of the system or may be supplied intermittently, such as on a puff by puff basis. The power may be supplied to the heater element in the form of pulses of electrical current.

The aerosol-generating device preferably comprises a user activated switch, for activating power to be supplied to the electrical heater.

The device preferably comprises at least one air inlet, and at least one air outlet, such that an air flow pathway is formed from the at least one air inlet to the at least one air outlet through the cavity. At least one wall of the cavity may be porous or may comprise an air inlet.

The aerosol-generating device preferably comprises a mouthpiece.

The device may further comprise a detector capable of detecting the presence of the sachet in the cavity and distinguishing the sachet from other sachets configured for use with the system. The detector may be used to control power to the electrical heater, such that no power may be supplied unless a sachet is detected in the cavity. Alternatively, or in addition, the detector may be configured to provide the controller with information on the type of sachet in the cavity such that an appropriate heating protocol can be used.

The heating protocol may comprise one or more of: a maximum operating temperature for the electrical heater, a maximum heating time per puff, a minimum time between puffs, a maximum number of puffs per sachet and a maximum total heating time for the sachet. Establishing a heating protocol tailored to the particular sachet is advantageous because the aerosol-forming substrates in particular sachets may require, or provide an improved smoking experience with, particular heating conditions. The electronic circuitry may be programmable, in which case various heating protocols may be stored and updated.

The sachet of aerosol-forming substrate may comprise at least one of: a taggant, having an identifiable spectroscopic signature, incorporated within a material of the sachet; and identification information printed on the sachet. The detector is preferably configured to distinguish the sachet in dependence on the taggant or on the printed identification information.

In one embodiment, the detector preferably is a spectroscopic detector comprising an optical sensor including at least one light emitter and at least one light sensor. Preferably, the light emitter is configured to emit infra-red wavelength light, or ultraviolet wavelength light. Preferably, the light sensor is configured to detect infra-red wavelength light, or ultraviolet wavelength light.

The taggant may comprise an identifiable spectroscopic signature in absorption. When the taggant is illuminated by the light source of the aerosol-generating device, the taggant will absorb a specific wavelength, or set of wavelengths, and the wavelengths of light subsequently received by the light sensor will therefore enable the aerosol-generating device to determine the taggant in dependence on the absent wavelengths.

The physical and chemical structure of the taggant can be controlled such that the absorbed wavelength of light can be set as required. In a preferred embodiment, the absorbed wavelength of light is not in the visible spectrum. Preferably, the absorbed wavelength is in the Infra-red or Ultraviolet range.

In addition, or instead of the taggant comprising an identifiable spectroscopic signature in absorption, the taggant may comprise an identifiable spectroscopic signature in emission. When the taggant is illuminated by the light source of the aerosol-generating device, the light preferably excites the taggant and emits at least one wavelength of light, shifted from the wavelength of the excitation light. As will be appreciated, this is a form of photoluminescence, and may be phosphorescence, or fluorescence. By controlling the physical and chemical structure of the taggant the spectroscopic signature can be controlled. In some embodiments, the identifiable signature may be in dependence on the time response of the emission in relation to the excitation, or the decay rate of the emission after excitation.

In a preferred embodiment, the wavelength of the emitted light is not in the visible spectrum. Preferably, the wavelength of the emitted light is in the Infra-red or Ultraviolet range.

In another embodiment, the detector comprises an optical sensor including at least one light emitter and at least one light sensor. In this embodiment, the detector may comprise one light emitter and one light sensor. Alternatively, the detector may comprise more than one light sensor in the form of a one dimensional (e.g. linear) array of light sensors. Furthermore, the detector may comprise more than one light sensor in the form of a two dimensional array of light sensors.

The identification information printed on the sachet may comprise one or more of: sachet type, aerosol-forming substrate type, date of production, place of production, batch number and other production details, and use-by date.

The identification information may be printed on the sachet in various forms. Various inks may be used for printing, including visible ink, ultra violet (UV) ink, infrared (IR) ink, phosphorescent ink, fluorescent ink and metallic ink.

According to a further aspect of the present invention, there is provided an electrically operated aerosol-generating system. The system comprises an electrically operated aerosol-generating device as described herein in accordance with the third aspect of the present invention and a sachet of aerosol-forming substrate as described herein in accordance with the first or second aspects of the present invention. The system may be an electrically operated smoking system. The system may be a handheld aerosol-generating system. The aerosol-generating system may have a size comparable to a conventional cigar or cigarette. The smoking system may have a total length between approximately 30 mm and approximately 150 mm. The smoking system may have an external diameter between approximately 5 mm and approximately 30 mm.

According to a yet further aspect of the present invention, there is provided a method of manufacturing a sachet of aerosol-forming substrate as described herein in accordance with the first or second aspects of the present invention. The method comprises: feeding a web of electrically conductive material; feeding aerosol-forming substrate pellets onto the web at regular intervals; feeding the combined web of material and pellets into a tube of material; and sealing the tube of material at regular intervals, the aerosol-forming substrate pellet being disposed between the seals, to form sealed sachets of aerosol-forming substrate, the web of electrically conductive material forming an electrical heater element in each sachet.

The method preferably further comprises cutting the tube at the sealing location to form individual sealed sachets of aerosol-forming substrate.

Alternatively, the method may further comprise providing a line of weakness at the sealing location to enable individual sachets of aerosol-forming substrate to be detached. The line of weakness may be a line of perforations extending across the width of the tube. The method may further comprise cutting the series of sachets to form groups of sachets having a plurality of sachets, such as two, three, four, five, six, seven, eight or more sachets, joined at lines of weakness.

The method may further comprise applying material to the web of electrically conductive material to form electrically conductive contact portions at regular intervals. The electrically conductive material is preferably applied in the cross-direction of the web. Alternatively, the electrically conductive material may be applied substantially continuously along the machine-direction of the web. In a yet further embodiment, the method may further comprise applying a staple of electrically conductive material adjacent each sealed end of a sachet to form electrically conductive contact portions at regular intervals.

As used herein, the term "machine-direction" refers to the direction in which the web of material travels along the process line. The term "cross-direction" refers to the direction orthogonal to the machine-direction.

The electrically conductive material may be formed from a mesh at least having electrically conductive filaments in the machine-direction, and wherein the electrical contacts are formed from electrically conductive filaments provided in the cross-direction, the electrically conductive filaments forming the electrical contacts having a first density of filaments and the electrically conductive filaments forming the mesh having a second density of filaments the first density being greater than the second density. The densities are preferably number densities.

The aerosol-forming substrate pellets may be fed onto the web by pressing, or deposited using slurry deposition.

Any feature in one aspect of the invention may be applied to other aspects of the invention, in any appropriate combination. In particular, method aspects may be applied to apparatus aspects, and vice versa. Furthermore, any, some and/or all features in one aspect can be applied to any, some and/or all features in any other aspect, in any appropriate combination.

It should also be appreciated that particular combinations of the various features described and defined in any aspects of the invention can be implemented and/or supplied and/or used independently.

The disclosure extends to methods and apparatus substantially as herein described with reference to the accompanying drawings.

The invention will be further described, by way of example only, with reference to the accompanying drawings in which:

FIG. 5 shows a manufacturing process for manufacturing sachets according to the present invention.

Figure 1:
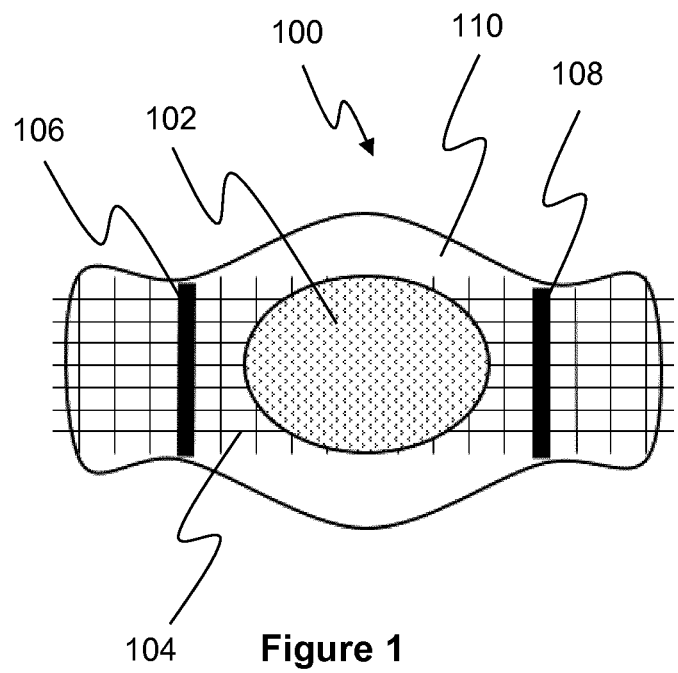
FIG. 1 shows a cut-away view of a sachet according to one embodiment of the present invention.
Figure 2:
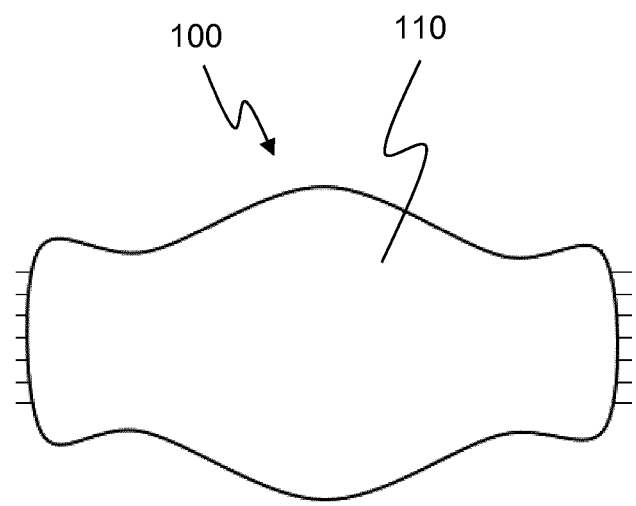
FIG. 2 shows the sachet of FIG. 1.

FIG. 1 shows a sachet 100 of aerosol-forming substrate for use in an electrically heated aerosol-generating device. The sachet 100 comprises a pellet 102 of aerosol-forming substrate, an electrical heater element 104, a first electrically conductive contact portion 106, and a second electrically conductive contact portion 108. The components of the sachet are housed within a container 110. FIG. 2 shows the external surface of the sachet container 110. As can be seen, the electrically conductive contact portions 106 and 108 are provided internally to the sachet 100.

The electrical heater element 104 is a mesh type heater formed from carbon fibre filaments, with a mesh size of about 120 Mesh US (about 120 filaments per inch). The filaments have a diameter of about 16 µm. The total resistance of the heater element is around 1 Ohm. The mesh is electrically coupled to the electrically conductive contact portions 106 and 108. The contact portions 106 and 108 are also formed of carbon fibre filaments. The filaments of the contact portions are more densely packed than the filaments in the mesh, and thus the electrical resistance of the contact portions 106 and 108 is at least an order of magnitude less than the resistance of the mesh, preferably at least two orders of magnitude less.

The aerosol-forming substrate comprises tobacco and an aerosol former such as polyhydric alcohol. The polyhydric alcohol is preferably propylene glycol or glycerine. In one embodiment, the tobacco is homogenised tobacco.

The aerosol-forming substrate, in the form of the pellet 102, is pressed onto the heater element, and is therefore directly engaged with the heater element. This reduces the power requirements of the device.

The aerosol-forming substrate pellet 102 and the heater element 104 are sealed in the container 110. The container 110 is a flexible foil material which is heat resistant at least up to the operating temperature of the device. The foil material in this example may be Nylon 6,6.

The sachet has a width of about 10 mm and a length of between about 12 mm and about 15 mm. The pellet 102 of aerosol-forming substrate has a mass between about 50 mg and about 400 mg.

In use, the sachet is heated in an aerosol-generating device to generate an aerosol as described in further detail below.

Figure 3:
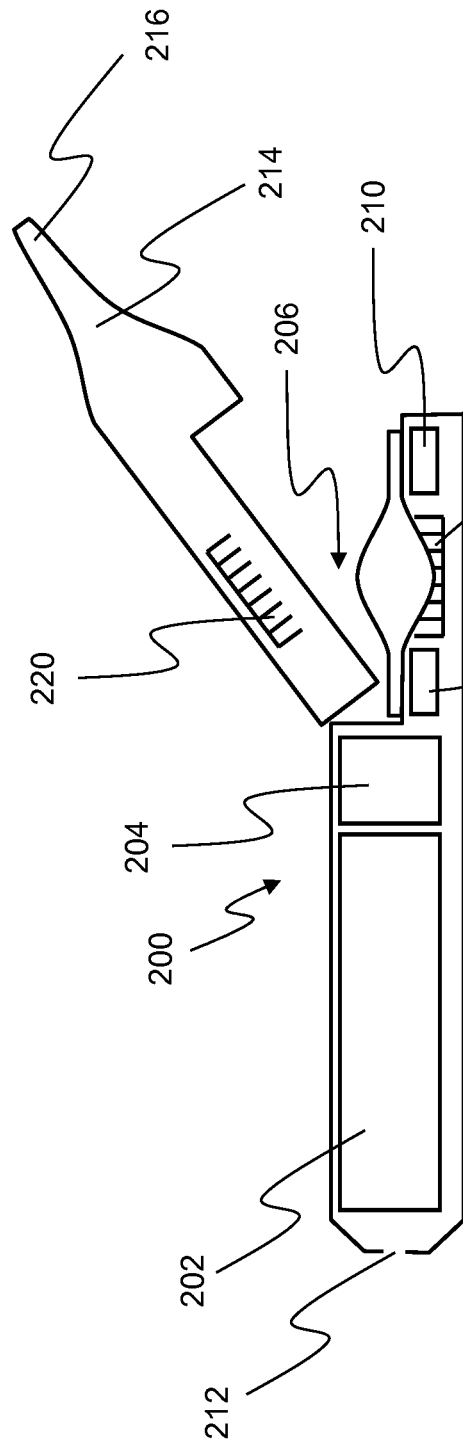
FIG. 3 shows an aerosol-generating device and a sachet according to one embodiment of the present invention.

FIG. 3 shows an electrically operated aerosol-generating device 200 used to heat the sachet to generate an aerosol. The aerosol-generating device 200 is portable and has a size comparable to a conventional cigar or cigarette. The device comprises an electrical power supply 202, such as a rechargeable battery, control circuitry 204, a cavity 206 for receiving a sachet 100 of aerosol-forming substrate, electrical contacts 208 and 210 disposed either side of the cavity 206 for receiving the sachet. The main housing of the device comprises an air inlet 212. The device further comprises a mouthpiece 214 comprising an air outlet 216. The mouthpiece 214 is provided on a movable hinged lid.

Figure 4:
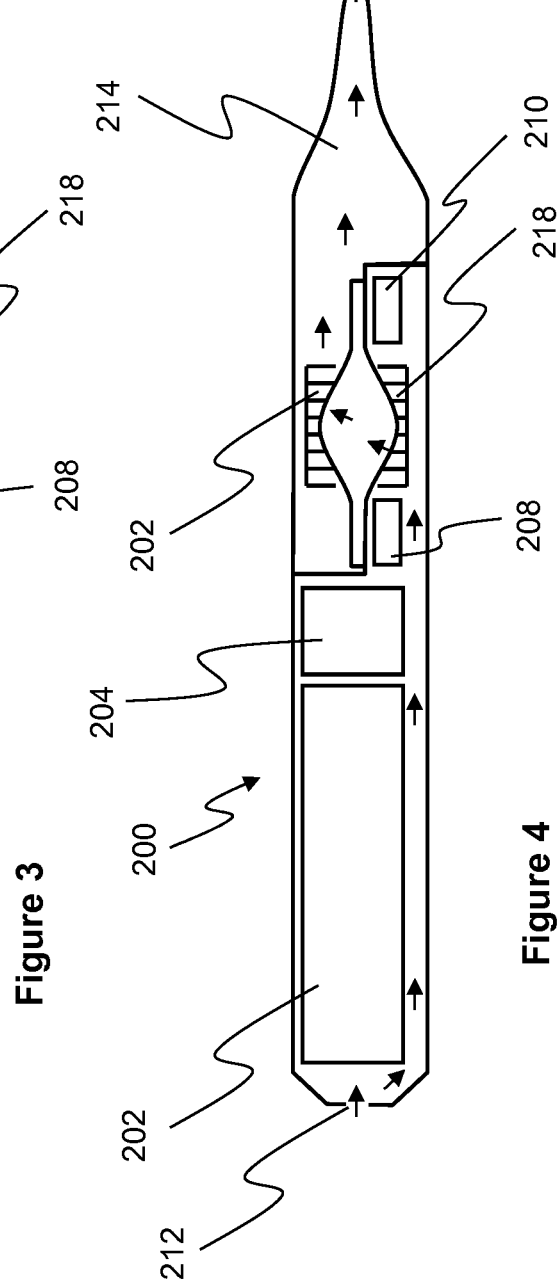
FIG. 4 shows the aerosol-generating device of FIG. 3 in use.

The cavity 206 comprises a plurality of piercing elements 218. The movable hinged lid also comprises a plurality of piercing elements 220. In use, with the lid in the first, open, position shown in FIG. 3, the user inserts the sealed sachet 100 into the cavity 206, and then moves the lid to the second, closed, position shown in FIG. 4. The lid is held in the closed position by magnets (not shown). Alternatively, a mechanical clasp or other such retaining device may be used. The piercing elements in the cavity and in the lid are hollow and are configured to pierce the sealed sachet to from an airflow pathway which extends through the hollow piercing elements and through the sachet. As shown in FIG. 4, the airflow pathway extends from the air inlet 212 along the device, through the hollow piercing elements 218 in the cavity 206, through the sachet 100, through the hollow piercing elements 220 and to the air outlet 216.

In addition to piercing the sachet, the lid is configured to both mechanically retain, and electrically couple the sachet to the device. The electrical contacts 208 and 210 are configured to be electrically coupled to the electrically conductive contact portions 106 and 108 of the sachet when the lid is in the second, closed, position. The electrical contacts 208 and 210 are configured to pierce the outer container of the sachet such that they directly contact the internal electrically conductive contact portions. The electrical contacts 208 and 210 may have serrations to more effectively pierce the sachet and contact the electrically conductive contact portions 106 and 108 respectively. In alternative embodiments, the contact portions of the sachet are external, and so the electrical contacts of the device are not required to pierce the sachet.

When the user activates the device, either by puffing on the mouthpiece to activate a puff sensor (not shown), or by activating a manual switch (not shown), the controller 204 is configured to provide power to the electrical heater element 104 from the power supply 206 to heat the sachet to the operating temperature. In a preferred example, the operating temperature is about 200 degrees C.

Once the sachet reaches the operating temperature the user draws on the mouthpiece, and air is drawn through the device from the air inlet 212, through the cavity 206 and sachet 100, and out of the air outlet 216 in the mouthpiece 214.

As shown in FIG. 5, the sachets may be manufactured in a linear manufacturing process. A web of material 300 comprising the mesh for the electrical heater element is fed from a bobbin of web material (not shown). At stage 302, the electrically conductive contact portions 304 are applied to the web material at regular intervals. At stage 306, the pellet of aerosol-forming substrate 308 is applied between the contact portions 304 by pressing the pellet onto the web material. As can be seen, the pellet of aerosol-forming substrate is applied between every other contact portion to leave a blank portion. At stage 310, the web material is then fed into a tube of material 312 to form the container of the sachet. The tube of material 312 is fed from a bobbin (not shown). The tube of material is then sealed 314 at stage 316 within the blank portion not containing the aerosol-forming substrate pellets. Finally, the tubular material is cut at stage 318 to form individual sealed sachets 100.

The invention claimed is:

1. An electrically operated aerosol-generating device, comprising:
a power supply;
electronic control circuitry;
a cavity configured to receive a sachet of aerosol-forming substrate, the sachet comprising:
an aerosol-forming substrate disposed within the sachet, and
an electrical heater element comprising first and second electrically conductive portions,
wherein the electrical heater element is disposed within the sachet and is in direct contact with the aerosol-forming substrate;
a sachet retainer configured to retain the sachet in the cavity;
at least one piercing element configured to pierce the sachet of aerosol-forming substrate when the sachet is received in the cavity; and
electrical contacts disposed adjacent the cavity and being configured to allow the first and the second electrically conductive portions of the electrical heater element to be electrically connected to the power supply,
wherein the sachet retainer is further configured to maintain electrical contact between the electrical heater element and the electrical contacts.

2. An electrically operated aerosol-generating device, comprising,
a power supply;
electronic control circuitry;
a cavity configured to receive a sachet of aerosol-forming substrate, the sachet comprising:
an aerosol-forming substrate disposed within the sachet, and
an electrical heater element comprising first and second electrically conductive portions,
wherein the electrical heater element is disposed within the sachet and is in direct contact with the aerosol-forming substrate,
a sachet retainer configured to retain the sachet in the cavity,
a first set of at least one piercing element and a second set of at least one piercing element, wherein the first set is configured to pierce a first side of the sachet and the second set is configured to pierce a second side of the sachet to form an airflow pathway through the sachet; and
electrical contacts disposed adjacent the cavity and being configured to allow the first and the second electrically conductive portions of the electrical heater element to be electrically connected to the power supply,
wherein the sachet retainer is further configured to maintain electrical contact between the electrical heater element and the electrical contacts.

3. The electrically operated aerosol-generating device according to claim 1, wherein the at least one piercing element is hollow, such that an airflow pathway is formed through the at least one piercing element and the sachet.

4. The electrically operated aerosol-generating device according to claim 2, wherein each of the first set of at least one piercing element and the second set of at least one piercing element is hollow, such that the airflow pathway is formed through the first set of at least one piercing element and the second set of at least one piercing element and the sachet.

5. The electrically operated aerosol-generating device according to claim 1, wherein the sachet retainer comprises a lid movable between a first position in which the sachet is insertable into the cavity, and a second position in which the sachet is retained in the cavity.

6. The electrically operated aerosol-generating device according to claim 2, wherein the sachet retainer comprises a lid movable between a first position in which the sachet is insertable into the cavity, and a second position in which the sachet is retained in the cavity.

* * * * *